United States Patent
Pelleter et al.

(10) Patent No.: US 6,242,615 B1
(45) Date of Patent: Jun. 5, 2001

(54) PROCESS FOR THE PREPARATION OF N-(3-HYDROXY-SUCCINYL)-AMINO ACID DERIVATIVES

(75) Inventors: Jacques Pelleter; Marie-Jeanne Pasquet; Thomas Geoffrey Colerick Bird, all of Reims (FR)

(73) Assignees: Zeneca Limited, London (GB); Zeneca Pharma S.A., Cergy Cedex (FR)

( * ) Notice: Subject to any disclaimer, the term of this patent is extended or adjusted under 35 U.S.C. 154(b) by 0 days.

(21) Appl. No.: 09/402,064

(22) PCT Filed: Mar. 25, 1998

(86) PCT No.: PCT/GB98/00913
§ 371 Date: Sep. 28, 1999
§ 102(e) Date: Sep. 28, 1999

(87) PCT Pub. No.: WO98/43946
PCT Pub. Date: Oct. 8, 1998

(30) Foreign Application Priority Data

Mar. 28, 1997 (EP) .................................. 97400724

(51) Int. Cl.$^7$ .................................. C07F 9/06; C07F 9/02
(52) U.S. Cl. ...................... 549/222; 558/145; 558/169
(58) Field of Search ............................. 549/222; 558/145, 558/169

(56) References Cited

U.S. PATENT DOCUMENTS 5,466,708 * 11/1995 Derungs et al. ........................ 514/449

FOREIGN PATENT DOCUMENTS 94 02446    2/1994   (WO) .

OTHER PUBLICATIONS

Bajwa J S et al: "Preparation of Chiral Substituted Succinic Acids" Journal of Organic Chemistry, vol. 48, No. 7 Apr. 1983, pp. 1114–1116, XP000615419 see p. 114; figure 8.
Miller M J et al: "Enantioselective Syntheses of 3–Substituted4–(Alkoxycarbonyl)–2–Azet Idinones From Malic Acid" Journal of Organic Chemistry, vol. 47, No. 25, Dec. 1982, pp. 4928–4933, XP000615420 see p. 4930; figures 20SS, 20RR.

Chemical Abstracts, vol. 12, No. 8, Apr. 20, 1918 Columbus, Ohio, US; "IV. Experiments with iodosuccinic acid" p. 808; XP002069979 see abstract & B. Holmberg: Arkiv Kemi Min. Geol., vol. 6, No. 23, 1917.

"Biochemicalien organische verbindingen en diagnostica (Sigma Catalogue)" 1996, Sigma Chemie XP002069977 Compounds C 5019, C5144 see p. 254.

"Biochemicalien organische verbindingen en diagnostica (Sigma Catalogue)" 1996, Sigma Chemie XP002069978 Coumpound B 4033 see p. 198.

M. Artico et al.: "Sintesi di beta–carbossi–beta–arilalanine" Il Farmaco, Edizione Scientifica, vol. XX, No. 7, 1965, Pavia It, pp. 523–531, XP002069975 see p. 530; table IV.

M. Artico: "Sintesi dell betacarbossitirosina" Il Farmaco, Edizione Scientifica, vol. XVii, No. 12, 1963, Pavia It, pp. 981–989, XP002069976 see p. 986, last paragraph—p. 987, paragraph 1.

* cited by examiner

Primary Examiner—Deborah C. Lambkin
(74) Attorney, Agent, or Firm—Pillsbury Winthrop LLP

(57) ABSTRACT

Processes for preparing compounds of the formula (I) are described: $P^1OOC—CH(OH)—CHR^1—CONH—Z$ wherein $P^1$ is hydrogen or a protecting group, Z is a group $—CHR^2COOP^2$ or $—CHR^2CONR^3R^4$ wherein $P^2$ is hydrogen or a protecting group and $R^1–R^4$ are values known in the TNF-inhibitor art. The compounds of the formula (I) are useful in inhibiting TNF and one or more matrix metalloproteinase enzymes. One intermediate in a process of the invention is formula (II).

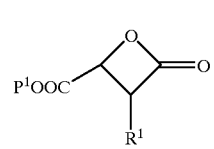

(II)

10 Claims, No Drawings

PROCESS FOR THE PREPARATION OF N-(3-HYDROXY-SUCCINYL)-AMINO ACID DERIVATIVES

This application is a 371 of PCT/GB98/00913 filed Mar. 25, 1998.

This invention relates to a chemical process and to chemical intermediates useful in such a process.

The chemical process of this invention is useful for preparing compounds which are inhibitors of the production of TNF (Tumour Necrosis Factor) which is believed to be formed by the cleavage of a pro-form, or larger precursor, by the enzyme pro-TNF Convertase. The chemical process of this invention is also useful for preparing compounds which are intermediates in the production of compounds which are inhibitors of the production of TNF.

Compounds which are inhibitors of the production of TNF will be useful in the treatment of disease or medical conditions in which excessive TNF production is known to give rise via a cascade of processes to a variety of physiological sequelae including the production of physiologically-active eicosanoids such as the prostaglandins and leukotrienes, the stimulation of the release of proteolytic enzymes such as collagenase, the activation of osteoclast activity leading to the resorption of calcium, the stimulation of the release of proteoglycans from, for example, cartilage, the stimulation of cell proliferations and to angiogenesis. It is also known that, in certain cellular systems, TNF production precedes and mediates the production of other cytokines such as interleukin-1 (IL-1) and interleukin-2 (IL-2) which are also believed to contribute to the pathology of disease states such as inflammatory and allergic diseases and cytokine-induced toxicity. Excessive TNF production has also been implicated in mediating or exacerbating the development of various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular disorders such as myocardial infarction, angina and peripheral vascular disease. Excessive TNF production has also been implicated in mediating complications of bacterial, fungal and/or viral infections such as endotoxic shock, septic shock and toxic shock syndrome. Excessive TNF production has also been implicated in mediating or exacerbating the development of adult respiratory distress syndrome, diseases involving cartilage or muscle resorption, Paget's disease and osteoporosis, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis.

The compounds able to be prepared by the process of this invention may also be inhibitors of one or more matrix metalloproteinases such as collagenases, stromelysins and gelatinases. Thus they may also be of use in the therapeutic treatment of disease conditions mediated by such enzymes for example arthritis (rheumatoid and osteoarthritis), osteoporosis and tumour metastasis.

The present invention relates, more specifically, to a process for preparing compounds of the formula (I):

wherein $P^1$ is hydrogen, a salt forming cation or a protecting group, Z is a group —$CHR^2COOP^2$ or —$CHR^2CONR^3R^4$ wherein $P^2$ is hydrogen or a protecting group and $R^1$–$R^4$ are values known in this structural type of TNF inhibitor.

The compounds of the formula (1), when Z is —$CHR^2CONR^3R^4$ and $P^1$ is hydrogen or a salt-formling cation are active TNF inhibitors.

The compounds of the formula (I) wherein $P^1$ is hydrogen or a salt-forming cation may also be converted to the corresponding hydroxamic acid of the formula (II):

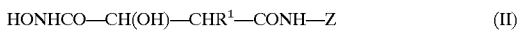

wherein $R^1$ and Z are as hereinbefore defined.

Compounds of the formulae (II) wherein Z is —$CHR^2CONR^3R^4$ are known TNF inhibitors. Compounds of the formula (II) wherein Z is —$CHR^2COOP^2$ may be converted to compounds of the formula (II) wherein Z is —$CHR^2CONR^3R^4$ by standard methods.

Compounds of the formnulae (I) and/or (II), wherein Z is —$CHR^2CONR^3R^4$ are disclosed as TNF inhibitors for example in: WO 9633165, WO 961693 1, WO 9606074, WO 9532944, WO 9519961, WO 9519957, WO 9519956, WO 9424140, WO 9402447, WO 9402446, WO 9533709, EPA 497192, EPA 236872, WO 9633176, WO 9633968, WO 9506031 and WO 9522966.

Accordingly the present invention provides a process for preparing a compound of the formula (I) or a salt thereof:

wherein $P^1$ is hydrogen or a protecting group;
Z is a group —$CHR^2COOP^2$ or —$CHR^2CONR^3R^4$ wherein $P^2$ is hydrogen or a protecting group and $R^1$–$R^4$ are values known in the afore-mentioned disclosures, which process comprises reacting a compound of the formula (III):

wherein L is a leaving group, with a compound of the formula (IV):

and thereafter if necessary:
i) removing any protecting groups,
ii) forming a salt.

L is a leaving group. Suitably L is a leaving group such as halo, for example chloro, bromo or iodo, or a sulphonyloxy group, such as $C_{1-6}$alkanesulphonyloxy for example methanesulphonyloxy, benzenesulphonyloxy or 4-methylbenzenesulphonyloxy.

The reaction between the compounds of the formulae (III) and (IV) is conveniently performed at a non-extreme temperature for example −25° C. to +50° C. and more conveniently 0° C. to +30° C. and most conveniently at ambient temperature.

The reaction is typically performed in a substantially inert organic solvent for example an aprotic solvent such as acetonitrile or diethyl ether.

The reaction of the compounds of the formulae (III) and (IV) is believed to proceed via the formation of the lactone of the formula (V).

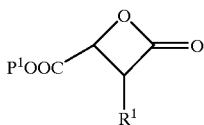

(V)

wherein $P^1$ and $R^1$ are as hereinbefore defined.

The compound of the formula (IV) acts as a base which is believed to convert the carboxylic acid function of the compound of the formula (III) to a carboxylate anion and which then displaces the leaving group L to form the lactone. The lactone is believed to be ring-opened by nucleophilic attack of the compound of the formula (IV) to form the compound of the formula (I).

Therefore another aspect of the present invention provides a process for preparing a compound of the formula (I) or salt thereof as hereinbefore defined which comprises reacting a lactone of the formula (V) with a compound of the formula (IV) and thereafter, if necessary, removing any protecting groups and/or forming a salt.

The reaction between the compounds of the formulae (IV) and (V) takes place under conditions analogous to those for the reaction of compounds of the formnulae (III) and (IV).

In another aspect the present invention provides a process for preparing a compound of the formula (V) as hereinbefore defined which comprises reacting a compound of the formula (III) with a non-nucleophilic base. In this way the base converts the carboxylic acid function of the compound of the formula (III) to a carboxylate anion which displaces L to form the lactone. However the non-nucleophilic base does not substantially react further with the lactone which may be isolated.

Suitable non-nucleophilic bases include both organic and inorganic bases.

Preferably the base is an inorganic base such as an alkali metal or alkaline earth metal carbonate or bicarbonate for example sodium bicarbonate, potassium carbonate, sodium carbonate or potassium bicarbonate. Suitably the reaction is performed under biphasic conditions with the compound of the formula (III) dissolved in an aprotic organic solvent such as acetonitrile, diethyl ether or dichloromethane which is stirred, typically vigorously, with an aqueous solution of the base at a non-extreme temperature for example at ambient temperature. The reaction may be monitored by thin layer chromatography or any other convenient methodology and, after a suitable period of time, the organic phase may be separated and worked-up to provide the compound of the formula (V). In an alternative the reaction is performed in the presence of a phase transfer catalyst for example benzyl trimethylammonium chloride, again with stirring at a non-extreme temperature.

In an alternative the non-nucleophilic base, for reacting with a compound of the formula (III), may be an organic base for example a tertiary amine such as di-isopropylethylamine. The reaction of a non-nucleophilic organic base with a compound of the formula (III) is typically performed under conditions analogous to those for the reaction of compound of the formulae (III) and (IV).

The present invention provides flexibility. In an advantageous aspect, it provides a "one-pot" reaction for preparing a compound of the formula (I) from the compounds of the formulae (III) and (IV). In another aspect, it can provide the compound of the formula (V) as a useful intermediate which can be reacted with a variety of compounds of the formula (IV).

The compounds of the formula (V) form another aspect of this invention.

Certain compounds of the formula (V) have been disclosed in the literature, in particular in the literature relating to polymers. Accordingly, the present invention provides a compound of the formula (VI):

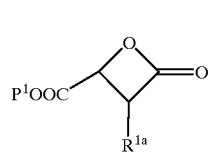

(VI)

wherein $P^1$ is hydrogen or a protecting group and $R^{1a}$ is a group $R^1$ as defined herein except that when $P^1$ is hydrogen, n-butyl, isopropyl, ethyl or allyl ($-CH_2CH=CH_2$), $R^{1a}$ is not hydrogen and when $P^1$ is benzyl, $R^{1a}$ is not hydrogen, methyl or isopropyl. In a particular aspect $R^{1a}$ is not hydrogen.

Preferably, in the compounds of the formula (VI), $P^1$ is benzyl or $C_{1-6}$alkyl, for example methyl, ethyl, n-propyl, n-propyl, isopropyl, n-butyl, isobutyl or tert-butyl.

Preferred values of $R^{1a}$ in the compounds of the formula (VI) are as described herein in relation to $R^1$ in the compounds of the formula (I).

Particular compounds of this invention include 3R-isobutyl-4-oxo-2S-oxetane carboxylic acid tert butyl ester and 3R-(4-benzyloxybutyl)-4-oxo-2S-oxetane carboxylic acid tert butyl ester.

In a preferred aspect, the process of the present invention provides compounds of the formula (Ia):

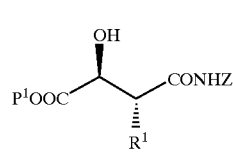

(Ia)

wherein $P^1$, $R^1$ and Z are as hereinbefore defined, from compounds of the formulae (III) and (IV). The reaction is believed to proceed via the formation of the lactone of the formula (Va):

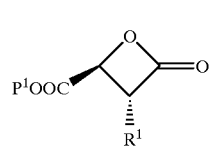

(Va)

wherein $P^1$ and $R^1$ are as hereinbefore defined. Preferred and particular values for $P^1$, $R^1$ and Z in the compounds of the formulae (Ia) and (Va) are as described for the compounds of the formulae (I) and (V) respectively. Thus in a further aspect the present invention provides the compounds of the formula (Va) wherein $R^1$ is $R^{1a}$ and $P^1$ and $R^{1a}$ are as defined as in relation to formula (VI) hereinabove.

The compounds of the formula (III) form another aspect of this invention. Certain compounds of the formula (III) have been disclosed in the literature.

Accordingly the present invention provides a compound of the formula (VII):

$$P^1OOC-CHL^1-CHR^1-COOH \quad (VII)$$

wherein $P^1$ is hydrogen or a protecting group, $R^1$ is as herein defined and $L^1$ is a sulphonyloxy group or halo except that:
i) when $P^1$ is hydrogen and $R^1$ is methyl or ethyl, $L^1$ is not bromo;
ii) when $P^1$ is hydrogen and $R^1$ is methyl, $L^1$ is not chloro;
iii) when $P^1$ is isopropyl and $R^1$ is methyl, $L^1$ is not chloro or iodo.

Preferably in the compounds of the formula (VII), $P^1$ is benzyl or $C_{1-6}$alkyl for example methyl, ethyl, n-propyl, isopropyl, n-butyl, isobutyl or tert-butyl.

Preferably $L^1$ is bromo, chloro or iodo.

Preferred values of $R^1$ in the compounds of the formula (VII) are as described herein in relation to $R^1$ in the compounds of the formula (I).

Particular compounds of this invention include 3R-chloro-2S-isobutylbutan-1,4-dioic acid 4-tert-butyl ester and 3R-chloro-2S-(4-benzyloxybutyl)butan-1,4-dioic acid 4-tert-butyl ester.

The compounds of the formula (III) may be prepared by reacting a dianion of the formula (VIII):

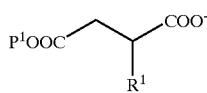

(VIII)

wherein $P^1$ and $R^1$ are as hereinbefore defined, with a source of the group L.

Suitable sources of halo include carbon tetrachloride and carbon tetrabromide.

Typically the dianion of the formula (VIII) is formed by reacting the corresponding neutral compound with a non-nucleophilic base, for example lithium di-isopropylamide at low temperatures (−78° C.) to form the dianion which is then reacted with the source of the group L.

The neutral compounds corresponding to the formula (VIII) are known in, or may be made by, the methods of the literature.

As stated hereinbefore the reaction of the compounds of the formulae (III) and (IV), or the reaction of the compounds of the formulae (IV) and (V), provides the compounds of the formula (I) or a salt thereof. The compounds of the formula (I) are optionally protected on the carboxylic acid function with a protecting group $P^1$.

The protecting group $P^1$ may in general be chosen from any of the groups described in the literature or known to the skilled chemist as appropriate for the protection of the carboxyl group, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxyl protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl); lower alkoxy lower alkyl groups (eg methoxymethyl, ethoxymethyl, isobutoxymethyl); lower aliphatic acyloxy lower alkyl groups. (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg benzyl, p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); and (2–6C) alkenyl groups (eg allyl and vinylethyl).

Methods particularly appropriate for the removal of carboxyl protecting groups include for example acid-, base-, metal- or enzymically-catalysed hydrolysis.

Any other functional group in the compounds of the formulae (III)–(V) may be protected as necessary. Such protecting groups may in general be chosen from any of the groups described in the literature or known to the skilled chemist as appropriate for the protection of the group in question, and may be introduced by conventional methods. Such protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Examples of hydroxyl protecting groups include lower alkyl groups (eg t-butyl), lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl); tri lower alkylsilyl (eg trimethylsilyl, t-butyldimethylsilyl) and aryl lower alkyl (eg benzyl) groups.

Examples of amino protecting groups include formyl, aralkyl groups (eg benzyl and substituted benzyl, p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl); trialkylsilyl (eg trimethylsilyl and t-butyldimethylsilyl); alkylidene (eg methylidene); benzylidene and substituted benzylidene groups.

Methods appropriate for removal of hydroxy and amino protecting groups include, for example, acid-, base-, metal- or enzymically-catalysed hydrolysis, for groups such as p-nitrobenzyloxycarbonyl, hydrogenation and for groups such as o-nitrobenzyloxycarbonyl, photolytically.

The compounds of the formula (I) wherein $P^1$ is hydrogen or an activated derivative thereof, optionally wherein the hydroxy group in —CH(OH)— is protected, may be reacted with hydroxylamine, O-protected hydroxylamine or a salt thereof (followed by deprotection as necessary) to provide the hydroxamic acid compounds of the formula (II) as hereinbefore described.

The compound of the formula (I) may be reacted in the form of the acid or an activated derivative thereof such as an acid halide, acid anhydride or an 'activated' ester such as 1H-benzo[1,2,3]triazol-1-yl, 1-hydroxy-benzo[1,2,3]triazole, pentafluorophenyl or 2,4,5-trichropheyl. The reaction of the compound of the formula (I) and hydroxylamine is performed under standard conditions. Typically the reaction of an activated ester of a compound of the formula (I) and hydroxylamine or O-protected hydroxylamine (for example protected with benzyl, t-butyl or silyl) is performed in the presence of a base, for example 2,6-lutidine in an anhydrous aprotic solvent, for example dimethylformamide, at a non-extreme temperature, for example in the region −30° to +25°, preferably about 0° C.

The processes of this invention may provide the compounds of the formula (I) in the form of a salt. In one aspect the compound is in the form of a pharmaceutically acceptable salt. Suitable pharmaceutically acceptable salts include acid addition salts such as hydrochloride, hydrobromide, citrate and maleate salts and salts formed with phosphoric and sulphuric acid. In another aspect suitable salts are base salts such as an alkali metal salt for example sodium or potassium, an alkaline earth metal salt for example calcium or magnesium, or organic amine salt for example triethylamine. In another aspect the compound is in the form of a non-pharmaceutically acceptable salt which may be a useful intermediate in preparing pharmaceutically acceptable salts of either of the compounds of the formula (I) or (II).

In the compounds of the formula (I), Z may be —CHR$^2$COOP$^2$ wherein P$^2$ is hydrogen or a protecting group. Such compounds may be deprotected (P$^2$ is hydrogen) and reacted with a compound of the formula (IX):

HNR$^3$R$^4$ (IX)

wherein R$^3$ and R$^4$ are as herein defined under standard peptide coupling conditions. Alternatively a corresponding compound of the formula (II) may be deprotected (P$^2$ is hydrogen) and reacted with a compound of the formula (IX) under standard peptide coupling conditions.

Thus in another aspect the present invention provides a process for preparing compounds of the formula (II) which comprises reacting compounds of the formulae (III) and (IV) (or compounds of the formulae (IV) and (V)) and, subsequently reacting the product with hydroxylamine, O-protected hydroxylamine or a salt thereof.

The compounds of the formulae (I) and (II) may be formulated and tested according to the methods of the literature.

In the compounds of the formulae (I) and (II), R$^1$–R$^4$ may have any value known for this structure in the TNF-inhibition literature and, in particular, known in the list of disclosures provided hereinbefore.

More particularly:
R$^1$ is alkyl; alkenyl; alkynyl; phenylalkyl; heteroarylalkyl; cycloalkylalkyl; cycloalkenylalkyl; phenylalkoxyalkyl; heteroarylalkoxyalkyl;
C$_{13-24}$ hydrocarbon chain optionally interrupted by one or more non-adjacent nitrogen, oxygen, sulphur, CO, SO, SO$_2$ groups;
R$^2$ is the characterising group of a non-natural α-amino acid in which any functional groups may be protected;
the side chain of a naturally occurring amino acid in which any functional groups may be protected;
CR$^x$R$^y$R$^z$ wherein each of R$^x$, R$^y$, R$^z$ is independently hydrogen, alkyl, alkenyl, alkynyl, phenylalkyl, halo, cyano, carboxy, alkoxycarbonyl, phenyl, heteroaryl, or R$^x$ and R$^y$ together with the carbon atom to which they are linked form a cycloalkyl or heterocyclic ring, or R$^x$, R$^y$ and R$^z$ together with the carbon atom to which they are linked form a bicyclic ring for example adamantyl;
phenyl, pyridyl, triazolyl, tetrazolyl, oxazolyl, isoxazolyl, pyrazolyl, thiopyrazolyl, isoxazolinyl, benzimidazolyl, benzoxazolyl or benzthiazolyl, any of which is optionally substituted;
R$^3$ is CHR$^a$R$^b$ wherein R$^a$ and R$^b$ independently represent phenyl or heteroaryl, which rings may be optionally linked by a bond or a C$_{1-4}$ alkylene or C$_{2-4}$alkenylene bridge, either of which may be interrupted by oxygen or sulphur;
—(Z—O)$_n$—Z wherein Z is C$_{1-6}$alkyl optionally interrupted by one or more non-adjacent sulphur or nitrogen atoms, n is >1;
C$_{3-8}$cycloalkyl or C$_{4-8}$cycloalkenyl; perfluoro C$_{1-4}$alkyl; alkyl; hydrogen; phenylalkyl; phenyl; heteroaryl; naphthyl;
R$^4$ is hydrogen or alkyl.

Suitably alkyl (in "alkyl" and in any term containing "alkyl") is C$_{1-12}$alkyl, preferably C$_{1-6}$alkyl. Suitably alkenyl is C$^{2-12}$alkenyl, preferably C$_{2-6}$alkenyl. Suitably alkynyl is C$_{2-6}$alkynyl. Suitably cycloalkyl is C$_{3-8}$cycloalkyl.

Any alkyl, cycloalkyl, cycloalkoxy, naphthyl, phenyl or heteroaryl ring is optionally substituted by one, two or three substituents selected from alkyl, alkoxy, alkylthio, phenoxy, phenylalkoxy, halo, cyano, carboxy, hydroxy, amino, alkylamino, dialkylamino, mercapto, alkylaminosulphonyl, dialkylaminosulphonyl, cyanoalkyl, aminoalkyl, alkanoylamino, alkoxycarbonylamino, alkanoyl, trifluoromethyl, alkanoylamino, aryl, phenyl, arylalkyl, aryloxy, arylalkoxy, heteroaryl, heteroarylalkyl, heterocyclyl, heterocyclylalkyl, alkoxycarbonyl, carbamoyl, alkylcarbamoyl, dialkylcarbamoyl, hydroxyethyl, perfluoroC$_{1-4}$alkyl, alkylsulphinyl, alkylsulphonyl, nitro, alkenyl, alkynyl, cycloalkyl, cycloalkenyl, benzyl, guanidine, pyrrolidino, morpholino or piperidino.

Favourably
R$^1$ is is hydrogen, C$_{1-8}$alkyl, C$_{2-6}$alkenyl, C$_{2-6}$alkynyl, C$_{3-8}$cycloalkyl, aryl, heteroaryl, heterocyclyl, arylC$_{1-6}$alkyl, heteroarylC$_{1-6}$alkyl, heterocyclylC$_{1-6}$alkyl or C$_{3-8}$cycloalkylC$_{1-6}$alkyl;
R$^2$ is C$_{1-6}$alkyl, C$_{2-6}$alkenyl, arylC$_{1-6}$alkyl, heteroarylC$_{1-6}$alkyl or the side-chain of a naturally occurring amino acid;
R$^3$ is hydrogen, C$_{1-6}$alkyl, C$_{3-8}$cycloalkyl, C$_{4-8}$cycloalkenyl, arylC$_{1-6}$alkyl, heteroarylC$_{1-6}$alkyl or heterocyclylC$_{1-6}$alkyl;
R$^4$ is hydrogen or C$_{1-6}$alkyl; or R$^3$ or R$^4$ together with the nitrogen atom to which they are joined form a heterocyclic ring;
wherein any group or ring, in R$^1$–R$^4$, is optionally substituted, and wherein "aryl in the terms "aryl" and "arylC$_{1-6}$alkyl" typically means phenyl or naphthyl, preferably phenyl, and "heteroaryl" in the terms "heteroaryl" and "heteroarylC$_{1-6}$alkyl" means an aromatic mono- or bicyclic 5–10 membered ring with up to five ring heteroatoms selected from nitrogen, oxygen and sulphur. (Examples of 'heteroaryl' include thienyl, pyrrolyl, firanyl, imidazolyl, thiazolyl, pyrimidinyl, pyridinyl, indolyl, benzimidazolyl, benzthiazolyl, quinolinyl and isoquinolinyl). "Heterocyclyl" in the term "heterocyclylC$_{1-6}$alkyl" means a non-aromatic mono- or bicyclic 5–10 membered ring with up to five ring hetero atoms selected from nitrogen, oxygen and sulphur. (Examples of "heterocyclyl" include pyrrolidinyl, morpholinyl, piperidinyl, dihydropyridinyl and dihydropyrimidinyl).

Any group or ring in $R^1$–$R^4$ may be optionally substituted, for example by up to three substituents which may be the same or different. Typical substituents include: hydroxy, $C_{1-6}$alkoxy for example methoxy, mercapto, $C_{1-6}$alkylthio for example methylthio, amino, $C_{1-6}$alkylamino for example methylamino, di-($C_{1-6}$alkyl)amino for example dimethylamino, carboxy, carbamoyl, $C_{1-6}$alkylcarbamoyl for example methylcarbamoyl, di-$C_{1-6}$alkylcarbamoyl for example dimethylcarbamoyl, $C_{1-6}$alkylsulphonyl for example methylsulphonyl, arylsulphonyl for example phenylsulphonyl, $C_{1-6}$alkylaminosulphonyl for example methylaminosulphonyl, di-($C_{1-6}$alkyl)aminosulphonyl for example dimethylamino-sulphonyl, nitro, cyano, cyano$C_{1-6}$alkyl for example cyanomethyl, hydroxy$C_{1-6}$alkyl for example hydroxymethyl, amino$C_{1-6}$alkyl for example aminoethyl, $C_{1-6}$alkanoylamino for example acetamido, $C_{1-6}$alkoxycarbonylamino for example methoxycarbonylamino, $C_{1-6}$alkanoyl for example acetyl, $C_{1-6}$alkanoyloxy for example acetoxy, $C_{1-6}$alkyl for example methyl, ethyl, isopropyl or tert-butyl, halo for example fluoro, chloro or bromo, trifluoromethyl, aryl for example phenyl, aryl$C_{1-6}$alkyl for example benzyl, aryloxy for example phenoxy, aryl$C_{1-6}$alkoxy for example benzyloxy, heteroaryl, heteroaryl$C_{1-6}$alkyl, heterocyclyl and heterocyclyl$C_{1-6}$alkyl. The term "side chain of a naturally occurring amino acid" means the side chain X of an amino acid $NH_2$—CHX—COOH. Suitable amino acids include alanine, arginine, aspartic acid, cysteine, asparagine, glutamine, histidine, homoserine, isoleucine, leucine, lysine, methionine, norleucine, norvaline, ornithine, serine, threonine, tryptophan, tyrosine and valine.

The compounds of the formulae (I) and (II) possess a number of chiral centres, at the carbon atom adjacent to the HONHOC— group, at —$CHR^2$—, at —$CHR^1$— (when $R^1$ is not hydrogen) and possibly in the variables $R^1$–$R^4$. The processes of the present invention may be used to prepare diastereoisomers and mixtures thereof that inhibit TNF Convertase and/or inhibit matrix metalloproteinase enzymes.

Favoured groups for $R^1$ include $C_{1-8}$alkyl for example isopropyl, n-propyl, isobutyl, sec-butyl, n-butyl, tert-butyl, isopentyl, n-pentyl, hexyl, heptyl or octyl; $C_{1-8}$alkyl interrupted by an oxygen or sulphur atom for example methoxypropyl, ethoxyethyl, propoxymethyl, ethylthioethyl or methylthiopropyl; phenyl$C_{1-6}$alkyl for example benzyl, phenethyl, phenylpropyl or phenylbutyl; aryl$C_{1-6}$alkyl interrupted by oxygen or sulphur for example benzyloxybutyl or benzyloxypropyl; $C_{3-8}$cycloalkyl for example cyclopropyl, cyclobutyl, cyclopentyl or cyclohexyl; aryl $C_{1-6}$alkyl interrupted by oxygen or sulphur for example benzyloxybutyl or benzyloxypropyl; or $C_{3-8}$cycloalkyl$C_{1-6}$alkyl for example cyclopropylmethyl, cyclopropylethyl, cyclobutylmethyl, cyclopentylmethyl or cyclohexylmethyl.

Preferably $R^1$ is isobutyl.

There is a chiral centre at —$CHR^1$— (when $R^1$ is not hydrogen); it is preferred that this centre has the configuration indicated in formula (X) hereinafter. For most values of $R^1$ this centre will have the R-stereochemistry under the Cahn-Prelog-Ingold sequence rules.

Favoured groups for $R^2$ include $C_{1-6}$alkyl for example methyl, ethyl, isopropyl, n-propyl, n-butyl, isobutyl, sec-butyl, tert-butyl, isopentyl, n-pentyl or hexyl; $C_{1-6}$alkyl interrupted by an oxygen or sulphur atom for example methoxyethyl, methoxypropyl, methylthioethyl or 1,1-dimethylmethylthiomethyl (MeSCMe$_2$—); or phenyl$C_{1-6}$alkyl for example benzyl or phenethyl.

Preferably $R^2$ is isobutyl, tert-butyl, 1,1-dimethylmethylthiomethyl or benzyl with tert-butyl being most preferred.

The chiral centre at —$CHR^2$— preferably has the configuration indicated in formula (X) hereinafter. For most of $R^2$ this centre will have the S-stereochemistry.

Favoured groups for $R^3$ include $C_{1-6}$alkyl for example methyl, ethyl, n-propyl, isopropyl, tert-butyl or n-butyl; $C_{1-6}$alkyl interrupted by an oxygen or sulphur atom for example hydroxyethyl, methoxyethyl, methylthioethyl or ethoxyethyl; $C_{2-6}$alkyl substituted by amino, $C_{1-6}$alkylamino or $C_{2-6}$dialkylamino; $C_{2-6}$alkyl substituted by either amino, $C_{1-6}$alkylamino or di-$C_{1-6}$alkylamino; phenyl$C_{1-6}$alkyl for example benzyl, phenethyl or phenylpropyl; heterocyclicalkyl for example 2-morpholinoethyl, 2-piperazinoethyl, 2-(N-methylpiperazino)ethyl or 2-piperidinoethyl; or $C_{3-8}$cycloalkyl$C_{1-6}$alkyl for example cyclopropylmethyl, cyclobutylmethyl or cyclopentylmethyl.

Preferably $R^3$ is methyl, ethyl, n-propyl, isobutyl, tert-butyl or benzyl. Of these methyl most preferred.

Favoured groups for $R^4$ are hydrogen and $C_{1-6}$alkyl for example methyl or ethyl. Preferably $R^4$ is hydrogen.

A particularly suitable class of compounds prepared by the processes of the present invention is that of formula (X):

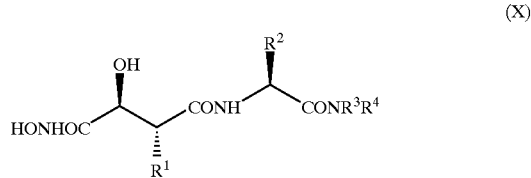

wherein $R^1$, $R^2$, $R^3$ and $R^4$ are as hereinbefore defined.

A preferred class of compound of the formula (X) is that wherein $R^1$ is isobutyl; $R^2$ is isobutyl, tert-butyl, 1,1-dimethylmethylthiomethyl or benzyl; $R^3$ is methyl, ethyl, n-propyl, isobutyl, tert-butyl, 2-dimethylaminoethyl or benzyl; and $R^4$ is hydrogen or methyl.

The following Examples illustrate the invention:
LDA means lithium di-isopropylamide
THF means tetrahydrofuran

EXAMPLE 1

$N^2$-[3S-Hydroxy-2R-isobutyl-4-tert-butyloxysuccinyl]-L-tert-leucine-$N^1$-methylamide a) To a stirred solution of LDA [45.5 mmol; prepared by addition of 2.5 M n-butyl lithium (18.2 ml, 45.5 mmol) in hexane to a solution of diisopropylamine (6.3 ml, 48.3 mmol) in dry THF (20 ml) at −78° C.] cooled to −78° C. under argon was added dropwise a solution of 2R-isobutyl-butan-1,4-dioic acid-4-tert-butyl ester[Ref1] (5.0 g, 21.7 mmol) in dry THF (15 ml). The mixture was stirred for 45 minutes at −78° C. and a solution of carbon tetrachloride (2.3 ml, 23.9 mmol) in dry THF (3 ml) was added slowly, dropwise over ca. 8 minutes avoiding that the internal temperature rise above −65° C. The mixture was allowed to stir at −78° C. for 30 minutes, warmed to room temperature and stirred for one hour at room temperature. The solution was cooled to −78° C. and quenched by addition of HCl (2N, 3.3 ml). The solution was warmed to room temperature and extracted with diethyl ether. The combined organic extracts were dried over MgSO$_4$, filtered and the solvents were removed to give directly one crude single isomer. The residue was purified by flash chromatography on silica using acetonitrile as eluant to give 3R-chloro-2S-isobutylbutan-1,4-dioic acid-4-tert-butyl ester (5.6 g, 98%) as a pale brown oil $^1$H-NMR (CDCl$_3$): 0.94 (d, 3H, J=4.8 Hz), 0.95 (d, 3H, J=4.8 Hz), 1.48 (s, 9H), 1.55 (m, 1H), 1.65–1.8 (m, 2H), 3.05–3.1 (m, 1H), 4.41 (d, 1H, J=8.1 Hz);

MS (EI): 264 (M{$^{35}$Cl}+H$^+$) and 266 (M{$^{37}$Cl}+H$^+$).

b) To a stirred solution of 3R-chloro-2S-isobutylbutan-1,4-dioic acid-4-tert-butyl ester (4.0 g, 15 mmol) in acetonitrile (100 ml) was added L-tert-leucine N-methylamide (2.8 g, 19.4 mmol). The mixture was stirred at room temperature for 24 hours. A further quantity of acetonitrile (25 ml) was added and the mixture stirred for 12 hours. The solvents were evaporated in vacuo and the residue partitioned between water and ethyl acetate. The combined organic extracts were dried over MgSO$_4$, filtered and the solvents were removed. The residue was purified by flash chromatography on silica using acetonitrile-dichloromethane (gradient from 1/4 to 1/3) as eluant to give N$^2$-[3S-hydroxy-2R-isobutyl-4-tert-butyloxysuccinyl]-L-tert-leucine-N$^1$methylamide (2.48 g, 45%) as a white solid:

$^1$NMR (CDCl$_3$): 0.92 (d, 3H, J=6.2 Hz), 0.96 (d, 3H, J=6.2 Hz), 0.99 (s, 9H), 1.47 (s, 9H), 1.55–1.75 (m, 3H), 2.75 (m, 1H), 2.79 (d, 3H, J=5.1 Hz), 3.73 (d, 1H, J=5.9 Hz), 4.1 (m, 1H), 4.13 (d, 1H, J=8.8 Hz), 5.88 (m, 1H), 6.68 (d, 1H, J=9.1 Hz);

MS (EI): 373 (M+H$^+$).

A small quantity of unreacted 3R-chloro-2S-isobutylbutan-1,4-dioic acid-4-tert-butyl ester (336 mg) was recovered from the chromatography.

EXAMPLE 2

3R-Isobutyl-4-oxo-2S-oxetane carboxylic acid tert-butyl ester

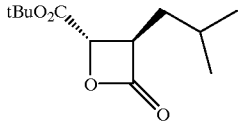

To a stirred solution of 3R-chloro-2S-isobutylbutan-1,4-dioic acid-4-tert-butyl ester (2.3 g, 8.7 mmol) in diethyl ether (50 ml) was added an aqueous solution (5%) of NaHCO$_3$ (45 ml) and the biphasic mixture was vigorously stirred at room temperature for 48 hours. The layers were separated and the organic phase was washed with water, dried over MgSO$_4$, filtered and the solvents were removed to give directly 3R-isobutyl-4-oxo-2S-oxetane carboxylic acid tert-butyl ester (1.3 g, 68%) as a brown oil:

$^1$H-NMR (CDCl$_3$): 0.94 (d, 3H, J=6.2 Hz), 0.98 (d, 3H, J=6.2 Hz), 1.52 (s, 9H), 1.7–1.85 (m, 3H), 3.7 (m, 1H), 4.47 (d, 1H, J=4.03 Hz);

MS (EI): 229 (M+H$^+$).

EXAMPLE 3

N$^2$-[3S-Hydroxy-2R-isobutyl-4-tert-butyloxysuccinyl]-L-tert-leucine-N$^1$-methylamide To a stirred solution of 3R-isobutyl-4-oxo-2S-oxetane carboxylic acid tert-butyl ester (1.2 g, 5.3 mmol) in acetonitrile (15 ml) was added L-tert-leucine N-methylamide (0.98 g 6.8 mmol). The mixture was stirred at room temperature for 36 hours. The solvents were evaporated in vacuo and the residue partitioned between water and diethyl ether. The combined organic extracts were dried over MgSO$_4$, filtered and the solvents were removed. The residue was purified by flash chromatography on silica using acetonitrile-dichloromethane (gradient from 1/9 to 3/7) as eluant to give N$^2$-[3S-hydroxy-2R-isobutyl-4-tert-butyloxysuccinyl]-L-tert-leucine-N$^1$-methylamide (1.27 g, 66%) as a white solid:

$^1$H-NMR (CDCl$_3$): 0.92 (d, 3H, J=6.2 Hz), 0.96 (d, 3H, J=6.2 Hz) 0.99 (s, 9H), 1.47 (s, 9H), 1.55–1.75 (m, 3H) 2.75 (m, 1H) 2.79 (d, 3H, J=5.1 Hz) 3.73 (d, 1H, J=5.9 Hz), 4.1 (m, 1H), 4.13 (d, 1H, J=8.8Hz), 5.88 (m, 1H), 6.68 (d, 1H, J=9.1 Hz);

MS (EI): 373 (M+H$^+$).

EXAMPLE 4

3R-Isobutyl-4-oxo-2S-oxetane carboxylic acid tert-butyl ester

To a stirred solution of 3R-chloro-2S-isobutyl-butan-1,4-dioic acid-4-tert-butyl ester (103 mg, 0.4 mmol) in dichloromethane (10 ml) was added an aqueous solution (10%) of NaHCO$_3$ (5 ml) followed by benzyl trimethylammonium chloride (7 mg, 0.04 mmol) and the biphasic mixture was vigorously stirred at room temperature for 9 hours. The layers were separated and the organic phase was washed with water, dried over MgSO$_4$, filtered and the solvents were removed to give directly 3R-isobutyl-4-oxo-2S-oxetane carboxylic acid tert-butyl ester (50 mg, 57%) as a pale brown oil:

$^1$H-NMR (CDCl$_3$): 0.94 (d, 3H, J=6.2 Hz), 0.98 (d, 3H, J=6.2 Hz), 1.52 (s, 9H), 1.7–1.85 (m, 3H), 3.7 (m, 1H), 4.47 (d, 1H, J=4.03 Hz).

EXAMPLE 5

N$^2$-[3S-Hydroxy-2R-isobutyl-4-tert-butyloxysuccinyl]-L-tert-leucine-N$^1$-dimethylamide In a manner analogous to that described in Example 1 (b), to a solution of 3R-chloro-2S-isobutylbutan-1,4-dioic acid-4-tert-butyl ester (500 mg, 1.89 mmol) in acetonitrile (7 ml) was added L-tert-leucine-N-dimethylamide$^{NOTE}$ (448 mg, 2.83 mmol). The mixture was stirred at room temperature for 24 hours. The mixture was poured into aqueous NH$_4$Cl (10%) and extracted with ethyl acetate. The combined organic extracts were washed with water, dried over MgSO$_4$, filtered and the solvents were removed. The residue was purified by flash chromatography on silica using acetonitrile-dichloromethane (1/4) as eluant to give N$^2$-[3S-hydroxy-2R-isobutyl-4-tert-butyloxysuccinyl]-L-tert-leucine-N$^1$-dimethylamide (395 mg, 54%) as a gum which solidified:

$^1$H-NMR (CDCl$_3$): 0.92 (d, 3H, J=5.5 Hz) 0.95 (d, 3H, J=5.8 Hz) 0.98 (s, 9H), 1.47 (s, 9H), 1.55–1.7 (m, 3H) 2.72 (m, 1H), 2.95 (s, 3H), 3.1 (s, 3H) 3.86 (s br, 1H), 4.07 (m, 1H), 4.86 (d, 1H, J=9.5 Hz), 6.61 (d, 1H, J=9.2 Hz);

MS (EI): 409 (M+Na$^+$).

$^{NOTE}$ L-tert-leucine-N-dimethylamide was prepared by the reaction of L-tert-leucine with triphosgene to give 3-(S)-tert-butyl oxazolidine-1,4-dione which was then treated with a saturated ethereal solution of dimethylamine.

EXAMPLE 6

N$^2$-[3S-Hydroxy-2R-isobutyl-4-tert-butyloxysuccinyl]-L-tert-leucine-N$^1$-(2-dimethylaminoethyl)amide In a manner analogous to that described in Example 1 (b), to a solution of 3R-chloro-2S-isobutylbutan-1,4-dioic acid- 4-tert-butyl ester (500 mg, 1.89 mmol) in acetonitrile (7 ml) was added L-tert-leucine-N-(2-dimethylaminoethyl) amide[NOTE] (455 mg, 2.2 mmol). The mixture was stirred at room temperature for 48 hours. The mixture was poured into aqueous $NH_4Cl$ (10%) and extracted with ethyl acetate. The combined organic extracts were washed with water, dried over $MgSO_4$, filtered and the solvents were removed. The residue was purified by flash chromatography on silica using methanol-dichloromethane (1/9) as eluant to give $N^2$-[3S-hydroxy-2R-isobutyl-4-tert-butyloxysuccinyl]-L-tert-leucine-$N^1$-(2-dimethylaminoethyl)amide(437 mg, 54%) as a gum:

$^1$H-NMR (CDC$_3$): 0.93 (d, 3H, J=5.8 Hz), 0.96 (d, 3H, J=6.2 Hz), 1.0 (s, 9H), 1.48 (s, 9H), 1.55–1.71 (m, 3H), 2.23 (s, 6H), 2.46 (m, 2H), 2.76 (m, 1H), 3.34 (m, 2H), 4.11 (d, 1H, J=3.3 Hz), 4.19 (d, 1H, J=9.2Hz), 6.6 (m, 2H);

MS (EI): 430 (M+H$^+$) and 452 (M+Na$^+$).

[NOTE] L-tert-leucine-2-dimethylaminoethylamide was prepared by the reaction of L-tert-leucine with triphosgene to give 3-(S)-tert-butyl oxazolidine-1,4-dione which was then treated with N,N-dimethyl ethylenediamine.

EXAMPLE 7

$N^2$-[3S-Hydroxy-2R-(4'-benzyloxy)butyl-4-tert-butyloxysuccinyl]-L-tert-leucine-$N^1$-methylamide In a manner analogous to that described in Example 1 (a), to a stirred solution of LDA [11.24 mmol; prepared by addition of 2.5 M n-butyl lithium (4.5 ml, 11.24 mmol) in hexane to a solution of diisopropylamine (1.57 ml, 11.24 mmol) in dry THF (4 ml) at −78° C.] cooled to −78° C. under argon was added dropwise a solution of 2R-(4'-benzyloxy) butyl-butan-1,4-dioic acid-4-tert-butyl ester[Ref2] (1.8 g, 5.35 mmol) in dry THF (2 ml). The mixture was stirred for 70 minutes at −78° C. and a solution of carbon tetrachloride (0.566 ml, 5.89 mmol) in dry THF (1 ml) was added slowly, dropwise over ca. 8 minutes avoiding that the internal temperature rise above −65° C. The mixture was allowed to stir at −78° C. for 60 minutes and quenched by addition of HCl (2N). The solution was warmed to room temperature and extracted with diethyl ether. The combined organic extracts were dried over $MgSO_4$, filtered and the solvents were removed to give directly crude 3R-chloro-2S-(4'-benzyloxy)butyl-butan-1,4-dioic acid-4-tert-butyl ester (2.13 g, 100%) as a brown oil used as such in the following step:

$^1$H-NMR (CDCl$_3$): 1.3–1.75 (m, 6H), 1.47 (s, 9H), 3.04 (m, 1H), 3.47 (t,2H, J=6.3 Hz), 4.37 (d, 1H, J=9.1 Hz), 4.49 (s, 2H), 7.29–7.34 (m, 5H);

MS (EI): 371 (M{$^{35}$Cl}+H$^+$) and 373 (M{$^{37}$Cl}+H$^+$).

In a manner analogous to that described in Example 1 (b), to a solution of 3R-chloro-2S-(4'-benzyloxy)butyl-butan-1,4-dioic acid-4-tert-butyl ester (1.9 g, 5.12 mmol) in acetonitrile (40 ml) was added L-tert-leucine-N-methylamide (738 mg, 6.15 mmol). The mixture was stirred at room temperature for 16 hours. The mixture was poured into aqueous $NH_4Cl$ (10%) and extracted with ethyl acetate. The combined organic extracts were washed with water, dried over $MgSO_4$, filtered and the solvents were removed. The residue was purified by flash chromatography on silica using acetonitrile-dichloromethane (gradient from 3/17 to 7/13) as eluant to give $N^2$-[3S-hydroxy-2R-(4'-benzyloxy)butyl-4-tert-butyloxysuccinyl]-L-tert-leucine-$N^1$-methylamide (520 mg, 27%) as a pale yellow gum:

$^1$H-NMR (CDCl$_3$): 0.98 (s, 9H), 1.46 (s, 9H), 1.6–1.9 (m, 6H), 2.66 (m, 1H), 2.7 (d, 3H, J=4.8 Hz), 3.46 (t, 2H, J=6.3 Hz), 3.74 (s br, 1H), 4.12 (m, 2H), 4.49 (m, 2H), 5.79 (m, 1H), 6.71 (d, 1H, J=9.2 Hz) 7.33–7.36 (m, 5H);

MS (EI): 479 (M+H$^+$).

A quantity of unreacted 3R-chloro-2S-(4'-benzyloxy) butyl-butan-1,4-dioic acid-4-tert-butyl ester (412 mg) was recovered from the chromatography.

REFERENCES

1. British Biotechnology Ltd (M. J. Crimmin, P. R. Beckett and M. H. Davis) PCT International Application WO 94/21625.
2. M. R. Gowravaram, J. S. Johnson, D. Delecki, E. R. Cook, B. E. Tomczuk, A. K. Ghose, A. M. Mathiowetz, J. C. Spurlino, B. Rubin et al., J. Med. Chem., 38(14), 2570–81, 1995.

What is claimed is:

1. A process for preparing a compound of the formula (I) or a salt thereof:

$$P^1OOC—CH(OH)—CHR^1—CONH—Z \quad (I)$$

having activity as a TNF-inhibitor when Z is a group —CHR$^2$CONR$^3$R$^4$, or an intermediate thereof when Z is a group —CHR$^2$COOP$^2$ convertible to a TNF-inhibitor when reacted with a compound of the formula (IX):

$$HNR^3R^4 \quad (IX);$$

wherein $P^1$ and $P^2$ are independently hydrogen or a protecting group, and $R^1$, $R^2$, $R^3$ and $R^4$ are independently substituents compatible with the TNF-inhibitor activity of the compound of formula (I) when Z is —CHR$^2$CONR$^3$R$^4$;

which process comprises reacting a compound of the formula (III):

$$P^1OOC—CHL—CHR^1—COOH \quad (III)$$

wherein $P^1$ and $R^1$ are as defined above, and L is a leaving group, with a compound of the formula (IV):

$$NH_2Z \quad (IV)$$

wherein Z is as defined above, and thereafter if necessary:
i) removing any protecting groups, and
ii) forming a salt.

2. A process for preparing a compound of the formula (I) or a salt thereof:

$$P^1OOC—CH(OH)—CHR^1—CONH—Z \quad (I)$$

having activity as a TNF-inhibitor when Z is a group —CHR$^2$CONR$^3$R$^4$, or an intermediate thereof when Z is a group —CHR$^2$COOP$^2$ convertible to a TNF-inhibitor when reacted with a compound of the formula (IX):

$$HNR^3R^4 \quad (IX);$$

wherein $P^1$ and $P^2$ are independently hydrogen or a protecting group, and $R^1$, $R^2$, $R^3$ and $R^4$ are independently substituents compatible with the TNF-inhibitor activity of the compound of formula (I) when Z is —CHR$^2$CONR$^3$R$^4$; which process comprises reacting a compound of the formula (V):

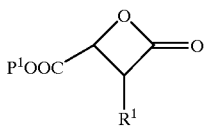

wherein $P^1$ and $R^1$ are as defined above with a compound of the formula (IV):

$$NH_2Z \qquad (IV)$$

wherein Z is as defined above, and thereafter if necessary:
i) removing any protecting groups, and
ii) forming a salt.

3. The process of claim 2 wherein the compound of formula (V) is prepared by a process comprising reacting a compound of the formula (VII):

$$P^1OOC\text{—}CHL^1\text{—}CHR^1\text{—}COOH \qquad (VII)$$

wherein $P^1$ and $R^1$ are as defined in claim 2 and $L^1$ is a leaving group, with a non-nucleophilic base.

4. A compound of the formula (VI):

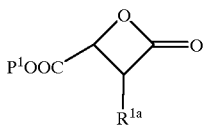

wherein $P^1$ is as defined in claim 1 and $R^{1a}$ is a group $R^1$ as defined herein except that when $P^1$ is n-butyl, isopropyl, ethyl or allyl (—$CH_2CH$=$CH_2$), $R^{1a}$ is not hydrogen and when $P^1$ is benzyl, $R^{1a}$ is not hydrogen, methyl or isopropyl.

5. A compound according to claim 4 which is of the formula (VIa):

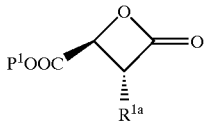

wherein $P^1$ and $R^{1a}$ are as defined in claim 4.

6. A compound according to either claim 4 or 5 wherein $R^{1a}$ is $C_{1-8}$alkyl, $C_{1-8}$alkyl interrupted by an oxygen or sulphur atom, phenyl$C_{1-6}$alkyl, aryl$C_{1-6}$alkyl interrupted by oxygen or sulphur, $C_{1-8}$cycloalkyl, aryl$C_{1-6}$alkyl interrupted by oxygen or sulphur or $C_{3-8}$cycloalkyl-$C_{1-6}$alkyl.

7. A compound according to claim 6 wherein $R^{1a}$ is isobutyl.

8. A compound according to claim 5 selected from the groups consisting of a $C_{1-6}$alkyl ester of 3R-isobutyl-4-oxo-2S-oxetane carboxylic acid and a $C_{1-6}$alkyl ester of 3R-(4-benzyloxybutyl)-4-oxo-2S-oxetane carboxylic acid.

9. A compound of the formula:

$$P^1OOC\text{—}CHL^1\text{—}CHR^1\text{—}COOH \qquad (VII)$$

wherein $P^1$ is hydrogen or a protecting group, $R^1$ is as defined in claim 1 and $L^1$ is a halo or sulphonyloxy group except that:
i) when $P^1$ is hydrogen and $R^1$ is methyl or ethyl, $L^1$ is not bromo;
ii) when $P^1$ is hydrogen and $R^1$ is methyl, $L^1$ is not chloro;
iii) when $P^1$ is isopropyl and $R^1$ is methyl, $L^1$ is not chloro or iodo.

10. A process for preparing a compound of the formula (II):

$$HONHCO\text{—}CH(OH)\text{—}CHR^1\text{—}CONH\text{—}Z \qquad (II)$$

wherein $R^1$ and Z are as defined in claim 1 which comprises:
i) reacting a compound of the formula (III) with a compound of the formula (IV) to form a compound of the formula (V):
ii) reacting the compound of the formula (V) wherein $P^1OOC$— is $HOOC$— or an activated derivative thereof with hydroxylamine, O-protected hydroxylamine or a salt thereof; and thereafter as necessary:
a) removing any protecting group;
b) forming a salt.

* * * * *